United States Patent [19]

Bradford et al.

[11] Patent Number: Plant 7,011

[45] Date of Patent: Sep. 5, 1989

[54] PLUM-APRICOT HYBRID TREE (RED VELVET PLUM-COT)

[76] Inventors: Norman G. Bradford, 11875 E. Savana Rd.; Lowell G. Bradford, 12439 E. Savana Rd., both of Le Grand, Calif. 95333

[21] Appl. No.: 220,833

[22] Filed: Jul. 18, 1988

[51] Int. Cl.[4] ..... A01H 5/00

[52] U.S. Cl. ..... Plt./38

[58] Field of Search ..... Plt. 38

*Primary Examiner*—Robert E. Bagwill

[57] ABSTRACT

The present invention relates to a plum-apricot hybrid tree and more particularly to a new and distinct variety broadly characterized by a medium size, vigorous, and hardy tree bearing very unique fruit. The fruit is similar to an apricot in outward appearance by having a typical apricot shape and skin pubescence, but differs from typical apricots by having a very dark purple skin color over its entire surface when mature. The fruit has a novel blend of both plum and apricot flavor, being acidic with an increasing amount of sugar with maturity. The fruit is of uniform large size, firm enough for shipping, and matures under the ecological conditions described approximately the last week in May, with first picking on May 20, 1988, making it an early ripening fruit compared with both plums and apricots. The variety was developed as the result of a seedling of an unknown plum as the seed parent and an unknown apricot as the per-chance pollen parent. Subsequent to origination of the present variety of plum-apricot hybrid tree, we asexually reproduced it by budding and grafting, and such reproduction of plant and fruit characteristics were true to the original plant in all respects.

1 Drawing Sheet

BACKGROUND OF THE VARIETY

The present invention relates to a new and distinct variety of plum-apricot hybrid tree, which has been denominated varietally as "Red Velvet Plum-Cot". The tree produces fruit that has a blend of both plum and apricot flavor and is somewhat similar to an apricot in external appearance by having typical apricot shape and pubescence. The fruit is large in size, firm enough for shipping, early in ripening compared to typical plum and apricot varieties, and unique from the typical apricot because it possesses full dark purple skin color at maturity.

In a continuing effort to improve the quality of shipping fruits, we, the inventors, typically grow a large number of plum and apricot seedlings each year. Many of the plum seedlings are crossed with specifically selected pollen while the remainder of them are allowed to be randomly pollinated and are planted as a mixed group of varying seed parents. Most of these chance plum seedlings are cross-pollinated by other plums, but occasionally they are crossed by an almond or an apricot. In 1984 we discovered this plum-apricot hybrid tree among our plantings of randomly pollinated plum seedlings, thereby being a seedling of an unknown plum as the seed parent and an unknown apricot as the per-chance pollen parent. It was discovered in the cultivated area of our experimental orchard at Bradford Farms near Le Grand, Calif. in Merced County (San Joaquin Valley).

Subsequent to origination of the present variety of plum-apricot hybrid tree, we asexually reproduced it by budding and grafting, and such reproduction of plant and fruit characteristics were true to the original plant in all respects.

DRAWING

The accompanying photograph shows the characteristics of the whole fruit in skin color and form, a characteristic fruit divided on its suture plane showing the flesh and stone, and typical leaves.

POMOLOGICAL CHARACTERISTICS

Referring now more specifically to the pomological characteristics of this new and distinct variety of plum-apricot hybrid tree, the following has been observed under the ecological conditions prevailing near Le Grand, Merced County (San Joaquin Valley), Calif., and was developed at the state of eating ripe on May 27, 1988. All major color code designations are by reference to the Inter-Society Color Council, National Bureau of Standards. Common color names are also used occasionally.

TREE

Size: Medium.
Vigor: Vigorous.
Growth: Spreading and dense.
Form: Round-topped.
Hardiness: Hardy.
Production: Medium productive.
Bearing: Uncertain bearer, not self-fruitful, and requires cross pollination by plums or apricots.
Trunk:
- *Size.*—Medium.
- *Texture.*—Shaggy.
- *Color.*—Blackish red [21. blackish R].
- *Lenticels.*—Numerous. Color: Moderate yellowish brown [77. m.yBr]. Size: 1/16" to ¼" [1.59–6.35 mm.].

Branches:
- *Size.*—Medium.
- *Texture.*—Shaggy.
- *Color.*—1st year wood — Topside: Dark red [16. d.R]. 1st year wood — Underside: Strong yellow green [117. s.YG]. Older wood: Grayish brown [61. gy.Br].
- *Lenticels.*—Numerous, small.

Leaves:

*Size.*—Medium. Average length: 3½" [88.90 mm.]. Average width: 2⅛" [53.98 mm.].
*Thickness.*—Medium.
*Form.*—Oval.
*Apex.*—Acuminate.
*Base.*—Acute.
*Surface.*—Smooth.
*Color.*—Dorsal surface: Dark yellowish green [137. d.yG]. Ventral surface: Moderate olive green [125. m.OlG].
*Margin.*—Finely crenate.
*Venation.*—Pinnately net veined.
*Petiole.*—Medium length and thickness. Average Length: ⅞" [22.23 mm.]. Average Thickness: 1/16" [1.59 mm.].
*Glands.*—Numbers: 2 to 4 per leaf. Position: Some oppositely and some alternately positioned on petiole and base of blade. Size: Medium. Form: Globose. Color: Deep reddish purple [238. deep rP].
*Stipules.*—Few. Average length: 3/16" [4.76 mm.].

Flower buds:
*Hardiness.*—Tender.
*Size.*—Medium.
*Length.*—Medium.
*Form.*—Free.
*Surface.*—Pubescent.

Flowers:
*Blooming period.*—Early, compared to apricots and plums.
*Size.*—Medium.
*Color.*—White [263. White].

FRUIT

Maturity when described: Eating ripe, May 27, 1988.
Date of first picking: May 20, 1988.
Date of last picking: May 27, 1988.
Size: Uniform, large.
*Average diameter axially.*—2⅛" [53.98 mm].
*Average transversely in suture plane:* 1¾" [44.45 mm].
Form: Uniform, symmetrical with respect to the suture, oblong, and compressed transversely toward the suture.
*Longitudinal section form.*—Oblong.
*Transverse section through diameter.*—Round.
Suture: An inconspicuous line that extends from the base but discontinues at the apex, has a characteristic slight hump just before apex, and has a slight depression at the pistil point.
Ventral surface: Rounded.
Lips: None.
Cavity: Rounded with suture showing on one side only.
Base: Slightly truncate.
Apex: Slightly depressed at pistil point.
Pistil point: Negligible in length.
Stem:
*Size.*—Medium.
*Average length.*—⅜" [9.53 mm.].
*Average width.*—⅛" [3.18 mm.].

Skin:
*Thickness.*—Medium.
*Texture.*—Tough.
*Tenacity.*—Tenacious to flesh.
*Skin flavor.*—Tart.
*Tendency to crack.*—Slight in wet season.
*Color.*—Dark purplish red [259. d.pR] over the entire surface.
*Down.*—Typical apricot pubescence and does not roll up when rubbed.

Flesh:
*Color.*—Brilliant yellow [83. brill.Y] from skin to pit.
*Amygdalin.*—Moderate.
*Juice.*—Moderate.
*Texture.*—Medium, fine, meaty.
*Fibers.*—Abundant, fine, and tender.
*Ripens.*—Evenly, but slightly earlier at the apex.
*Flavor.*—Acidic, but balanced with sugar when eating ripe.
*Aroma.*—Slight.
*Eating quality.*—Excellent, if not picked immaturely.

STONE

Type: Clingstone.
Form: Oval.
Base: Straight.
Apex: Rounded.
Sides: Equal.
Surface: Typical apricot surface.
Ridges: Has a characteristic pair of continuous ridges on each side of the dorsal fin from base to apex.
Color: Light Orange Yellow [70. l.OY].
Thickness of pit wall: 3/32" [2.38 mm.].
Tendency to split: Slight.
Kernel:
*Form.*—Ovate.
*Taste.*—Slightly bitter.
*Viable.*—Yes.
*Average width.*—¾" [19.05 mm.].
*Average length.*—1 1/16" [26.99 mm.].
Pellicle color: Moderate yellowish brown [77. m.yBr].
Amygdalin: Scant.

USE

Market: Fresh and long distance shipping.
Keeping quality: Medium.
Shipping quality: Medium.
Resistance to insects: No unusual susceptibilities noted.
Resistance to diseases: Susceptible to blossom brown-rot.
Resistance to frost: Blossoms are very susceptible to frost.

Although the new variety of plum-apricot hybrid tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct plum-apricot hybrid variety of fruit tree substantially as illustrated and described, whose fruit is similar to an apricot in outward appearance by having typical apricot shape and skin pubescence, but differs from typical apricots by having a very dark purple skin color over its entire surface at maturity, its fruit also has a novel blend of both plum and apricot flavor, being acidic with an increasing amount of sugar with maturity, is early ripening, maturing 5 days before the Red Beaut Plum (U.S. Plant Pat. No. 2,539), and is firm enough for shipping, therefore offering a very early and unique product not presently seen on typical supermarket shelves in America.

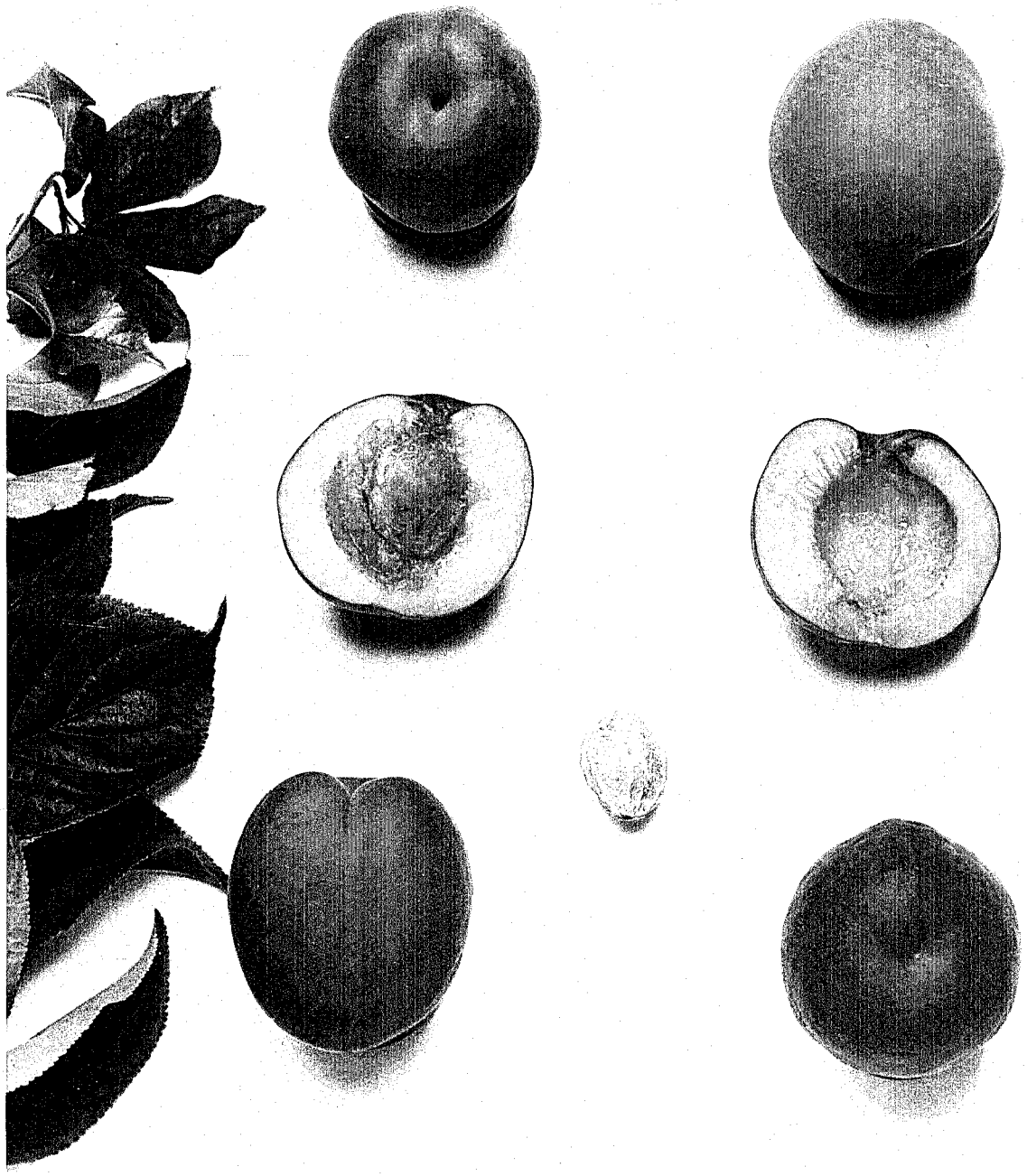

* * * * *